(12) United States Patent
Kline

(10) Patent No.: US 7,445,601 B2
(45) Date of Patent: Nov. 4, 2008

(54) NON-INVASIVE DEVICE AND METHOD FOR THE DIAGNOSIS OF PULMONARY VASCULAR OCCLUSIONS

(75) Inventor: Jeffrey A. Kline, Charlotte, NC (US)

(73) Assignee: Charlotte-Mecklenburg Hospital, Charlotte, NC (US)

( * ) Notice: Subject to any disclaimer, the term of this patent is extended or adjusted under 35 U.S.C. 154(b) by 867 days.

(21) Appl. No.: 10/816,279

(22) Filed: Apr. 1, 2004

(65) Prior Publication Data

US 2004/0210154 A1      Oct. 21, 2004

Related U.S. Application Data

(60) Continuation-in-part of application No. 10/400,339, filed on Mar. 26, 2003, now Pat. No. 7,083,574, which is a division of application No. 09/965,303, filed on Sep. 27, 2001, now Pat. No. 6,575,918.

(51) Int. Cl.
    *A61B 5/02*      (2006.01)
(52) U.S. Cl. ....................................... 600/532; 600/529
(58) Field of Classification Search ....................... None
    See application file for complete search history.

(56) References Cited

U.S. PATENT DOCUMENTS 3,799,149 A * 3/1974 Rummel et al. ............. 600/531
3,896,792 A * 7/1975 Vail et al. .................... 600/532
3,951,607 A * 4/1976 Fraser .......................... 422/84
4,966,141 A * 10/1990 Bacaner et al. ........ 128/207.14
5,515,859 A * 5/1996 Paz ........................ 250/339.13
5,533,512 A 7/1996 Novotny et al.
5,787,885 A * 8/1998 Lemelson ................... 600/309
6,084,682 A * 7/2000 Zare et al. ................... 356/437
6,099,481 A * 8/2000 Daniels et al. .............. 600/538
6,139,506 A * 10/2000 Heinonen ................... 600/532
7,192,782 B2 * 3/2007 Roller et al. ................ 436/116
2004/0236244 A1 * 11/2004 Allen et al. ................. 600/532

* cited by examiner

*Primary Examiner*—Robert L Nasser
(74) *Attorney, Agent, or Firm*—George R. McGuire; Bond Schoeneck & King, PLLC

(57) ABSTRACT

The invention involves a device and method for ascertaining the functioning of the respiratory system and determining the cause of abnormal respiratory function. The device comprises an apparatus for measuring the flow of air from a patient's breadth and determining the concentration of gases contained therein via real-time spectrometry. From this data, a processor computes the ratio of detected gases relative to each other and as a function of expired volume and plots the calculations on a display screen. Based on various plots, a physician can more easily estimate the probability of a number of pulmonary diseases and afflictions, such pulmonary embolism, emphysema, congestive heart failure, infection, and related problems.

19 Claims, 9 Drawing Sheets

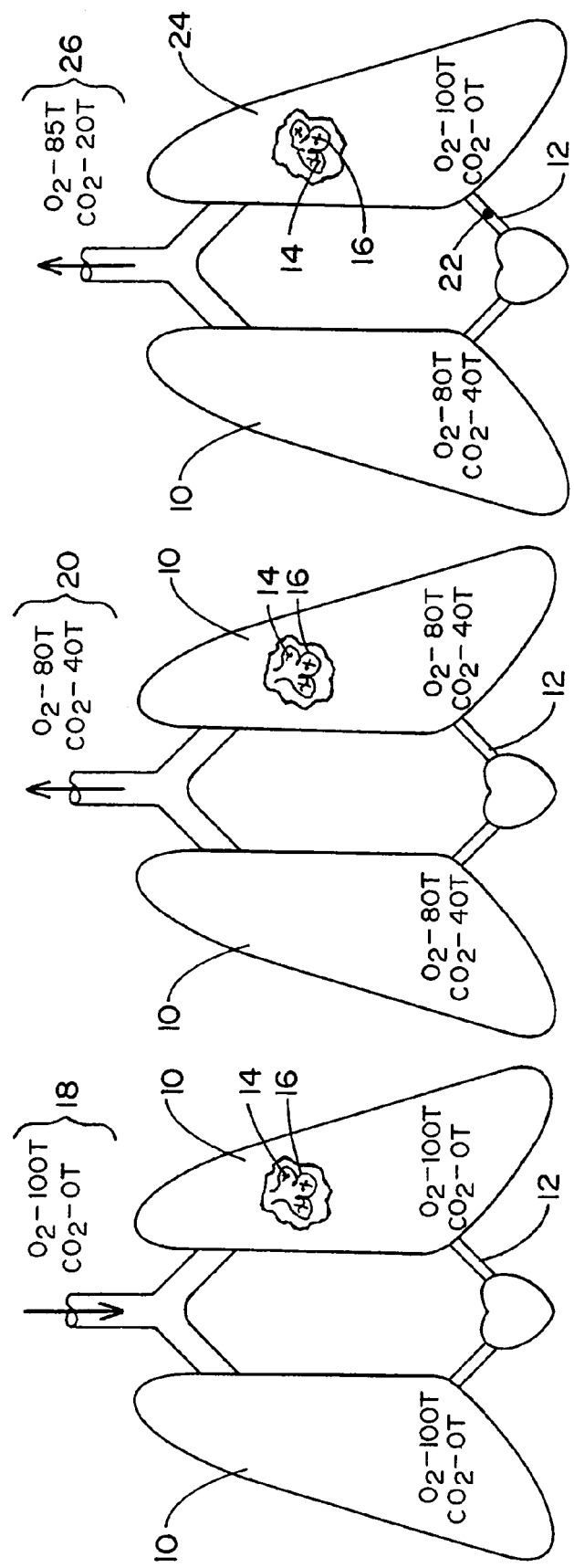

NON-INVASIVE DEVICE AND METHOD FOR THE DIAGNOSIS OF PULMONARY VASCULAR OCCLUSIONS

CROSS REFERENCES TO RELATED APPLICATION

The present application is a continuation-in-part of Applicant's U.S. application Ser. No. 10/400,339, filed on Mar. 26, 2003, now U.S. Pat. No. 7,083,574 which is a divisional application of Ser. No. 09/965,303, now U.S. Pat. No. 6,575,918, filed on Sep. 27, 2001.

BACKGROUND OF THE INVENTION

1. Field of Invention

The present invention relates generally to improvements in technology used in the field of vascular occlusions of the respiratory system, and more particularly to non-invasive devices and methods for the diagnosis of a pulmonary embolism and related disorders.

2. Description of Prior Art

A pulmonary embolism occurs when an embolus becomes lodged in lung arteries, thus blocking blood flow to lung tissue. An embolus is usually a blood clot, known as a thrombus, but may also comprise fat, amniotic fluid, bone marrow, tumor fragments, or even air bubbles that block a blood vessel. Unless treated promptly, a pulmonary embolism can be fatal. In the United States alone, around 600,000 cases occur annually, 10 percent of which result in death.

The detection of a pulmonary embolism is extremely difficult because signs and symptoms can easily be attributed to other conditions and symptoms may vary depending on the severity of the occurrence. Frequently, a pulmonary embolism is confused with a heart attack, pneumonia, hyperventilation, congestive heart failure or a panic attack. In other cases, there may be no symptoms at all.

Often, a physician must first eliminate the possibility of other lung diseases before determining that the symptoms, if any, are caused by a pulmonary embolism. Traditional diagnostic methods of testing involve blood tests, chest X-rays, and electrocardiograms. These methods are typically more effective in ruling out other possible reasons than for actually diagnosing a pulmonary embolism. For example, a chest x-ray may reveal subtle changes in the blood vessel patterns after an embolism and signs of pulmonary infarction. However, chest x-rays often show normal lungs even when an embolism is present, and even when the x-rays show abnormalities they rarely confirm a pulmonary embolism. Similarly, an electrocardiogram may show abnormalities, but it is only useful in establishing the possibility of a pulmonary embolism.

As a pulmonary embolism alters the ability of the lungs to oxygenate the blood and to remove carbon dioxide from the blood, one method of diagnosing the condition involves taking a specimen of arterial blood and measuring the partial pressure of oxygen and carbon dioxide in the arterial blood (i.e., an arterial blood gas analysis). Although a pulmonary embolism usually causes abnormalities in these measurements, there is no individual finding or combination of findings from the arterial blood gas analysis that allows either a reliable way to exclude or specific way of diagnosing pulmonary embolism. In particular, at least 15-20% of patients with a documented pulmonary embolism have normal oxygen and carbon dioxide contents of the arterial blood. Accordingly, the arterial blood analysis cannot reliably include or exclude the diagnosis of a pulmonary embolism.

The blood D-dimer assay is another diagnostic method that has become available for commercial use. The D-dimer protein fragment is formed when fibrin is cleaved by plasmin and therefore produced naturally whenever clots form in the body. As a result, the D-dimer assay is extremely sensitive for the presence of a pulmonary embolism but is very nonspecific. In other words, if the D-dimer assay is normal, the clinician has a reasonably high degree of certainty that no pulmonary embolism is present. However, many studies have shown a D-dimer assay is only normal in less than ⅓ of patients and thus produces a high degree of false positives. As a result, the D-dimer assay does not obviate formal pulmonary vascular imaging in most patients with symptoms of a pulmonary embolism.

In an attempt to increase the accuracy of diagnostic, physicians have recently turned to methods which can produce an image of a potentially afflicted lung. One such method is a nuclear perfusion study which involves the injection of a small amount of radioactive particles into a vein. The radioactive particles then travel to the lungs where they highlight the perfusion of blood in the lung based upon whether they can penetrate a given area of the lung. While normal results can indicate that a patient lacks a pulmonary embolism, an abnormal scan does not necessarily mean that a pulmonary embolism is present. Nuclear perfusion is often performed in conjunction with a lung ventilation scan to optimize results.

During a lung ventilation scan, the patient inhales a gaseous radioactive material. The radioactive material becomes distributed throughout the lung's small air sacs, known as alveoli, and can be imaged. By comparing this scan to the blood supply depicted in the perfusion scan, a physician may be able to determine whether the person has a pulmonary embolism based upon areas that show normal ventilation but lack sufficient perfusion. Nevertheless, a perfusion scan does not always provide clear evidence that a pulmonary embolism is the cause of the problem as it often yields indeterminate results in as many as 70% of patients.

Pulmonary angiograms are popular means of diagnosing a pulmonary embolism, but the procedure poses some risks and is more uncomfortable than other tests. During a pulmonary angiogram, a catheter is threaded into the pulmonary artery so that iodine dye can be injected into the bloodstream. The dye flows into the regions of the lung and is imaged using x-ray technology, which would indicate a pulmonary embolism as a blockage of flow in an artery. Pulmonary angiograms are more useful in diagnosing a pulmonary embolism than some of the other traditional methods, but often present health risks and can be expensive. Although frequently recommended by experts, few physicians and patients are willing to undergo such an invasive procedure.

Spiral volumetric computed tomography is another diagnostic tool that has recently been proposed as a less invasive test which can deliver more accurate results. The procedure's reported sensitivity has varied widely, however, and it may only be useful for diagnosing an embolism in central pulmonary arteries as it is relatively insensitive to clots in more remote regions of the lungs.

These pulmonary vascular imaging tests have several disadvantages in common. Nearly all require ionizing radiation and invasiveness of, at a minimum, an intravenous catheter. The imaging tests also typically involve costs of more than $1,000 for the patient, take more than two hours to perform, and require special expertise such as a trained technician to perform the tests and acquire the images and a board-certified radiologist to interpret the images. Notably, none are completely safe for patients who are pregnant. As a result of these shortcomings, the imaging procedures are not available in many outpatient clinic settings and in many portions of third world countries.

Nitric oxide (NO) is a clear colorless gas, produced naturally by enzymatic action on endogenous amino acids and molecular oxygen. Nitric oxide causes dilation of blood vessels, including the precapillary pulmonary arteries. It is well established that NO production generally increases in a plurality of mammalian tissues in response to a plurality of insults. Acute pulmonary embolism that causes obstruction of the pulmonary arteries represents a notable exception. Pulmonary embolism also causes direct obstruction of pulmonary vasculature, which leads to immediate elevation in pulmonary arterial pressures. This increase in pressure causes greater hydraulic shear forces to be exerted on erythrocytes as they are pumped out of the right ventricle into the lung and through the open lung arteries. Increased shear forces cause intravascular, intrapulmonary hemolysis, which leads to a release of free hemoglobin. The heme moiety of hemoglobin can bind NO, thereby causing a decrease in the concentration of NO in expired breath. Free hemoglobin is eventually degraded by intrapulmonary macrophages, through a catabolic pathway that liberates bilirubin and CO. Thus, intrapulmonary hemolysis consequent to pulmonary vascular obstruction causes decrease in lung NO content and an increase in CO content.

Testing also suggests that induction of either mild or severe pulmonary vascular occlusion in rats causes no increase in the transcription of the enzyme inducible nitric oxide synthase, the enzyme primarily responsible for producing nitric oxide in lung tissues. However, pulmonary vascular occlusion causes a dose-dependent increase in transcription of heme-oxygenase, also known as HO-1. Heme-oxygenase is the primary endogenous source of carbon monoxide (CO).

It is well established that exhaled concentrations of NO increase with many types of inflammatory lung disease, while the exhaled concentrations of CO have a more variable response, to some extent depending upon whether the patient is a smoker. In general, few diseases cause a simultaneous decrease in NO and increase in CO. A notable exception is the effect of smoking in the setting of chronic obstructive lung disease (COPD). This combination is known to decrease NO and increase CO. However, COPD produces a specific pattern and slope of the expired $CO_2$, $O_2$, and $CO_2/O_2$ ratio when these values are plotted as a function of expired volume on a dynamic basis. Mathematical and visual analysis of these curves allow distinction of COPD and other causes of airway obstruction from pulmonary vascular occlusion. A key drawback to the isolated measurement of NO is its lack of correspondence with clinical severity. The addition of the measurement of the $CO_2/O_2$ ratio as an index of hypoventilation, together with the dynamic plot of this ratio will improve the diagnostic accuracy of exhaled NO.

Moreover, certain treatments for a patient with pulmonary vascular occlusions are aimed at increasing concentrations of NO in both the acute and chronic setting. Pulmonary vascular occlusion can be associated with regional pre-capillary vascoconstriction, a reversible process that worsens the severity of mechanical pulmonary vascular obstruction. Pharmacological agents can be infused, ingested or inhaled that are specifically designed to enhance the intrapulmonary concentration and vasodilatory effect of NO in the lung vasculature. Continuous measurement of the $CO_2:O_2$ ratio while "spot checking" the expired NO concentration will provide a method to simultaneously determine bioavailability and physiological response of the lung to an treatment designed to increase intrapulmonary NO concentration for a patient with a process causing pulmonary vascular occlusion (see, e.g, U.S. Pat. No. 5,968,911 to Lawson, U.S. Pat. No. 5,839,433 to Higenbottam, and U.S. Pat. No. 5,823,180 to Zapol). Typical exhaled concentrations of NO associated with a therapeutic response are in the 10-300 parts per million range, whereas an increase in the $CO_2:O_2$ ratio above 40% (0.40) is associated with decrease in pulmonary vascular resistance.

Exhaled ozone ($O_3$) represents an additional inorganic molecule that indicates airway inflammation. Ozone inhaled from the ambient atmosphere is known to induce oxidative damage to lungs, and the amount of inhaled ozone increases in proportion to isprenoid markers of airway inflammation. In this classic scenario, the exhaled concentration of ozone is lower than the inhaled concentration, reflecting the consumption of ozone during oxidation of lung tissue substrates. However, under certain pathological conditions marked by oxidant damage, the lung may produce ozone, such that the exhaled concentration exceeds the inhaled concentration.

At least one device measures expired NO using laser spectroscopy. This device reports the concentration of NO and the concentration of $CO_2$ per breath for the purpose of diagnosing asthma exacerbations. The device does not measure CO, or $O_2$, however, and does not compute and display the concentration of NO as a function of the $CO_2/O_2$, or vise versa, either on a dynamic breath-to-breath basis or as an average point estimate.

OBJECTS AND ADVANTAGES

It is a principal object and advantage of the present invention to provide a system for measuring the concentrations of gases exhaled by a patient.

It is an additional object and advantage of the present invention to provide a system for displaying the concentration of gases exhaled by a patient.

It is a further object and advantage of the present invention to provide a system for assisting in the diagnosis of respiratory diseases by measuring and displaying the concentration and ratios of gases exhaled by a patient.

Other objects and advantages of the present invention will in part be obvious, and in part appear hereinafter.

SUMMARY OF THE INVENTION

In accordance with the foregoing objects and advantages, the present invention provides a device and method for non-invasively diagnosing a pulmonary embolism. The device of the present invention comprises a breathing tube having sensors for measuring the flow of air into and out of a patient's lungs while a remote data processing unit interconnected to the breathing tube simultaneously determines the oxygen and carbon dioxide concentrations. The device further includes a display screen for visually graphing the resulting calculations and providing a visual means for determining the likelihood that a pulmonary embolism is present based upon a change in measured gas concentrations. The additional measurement of NO, CO and $O_3$ will enhance the ability of the present invention to diagnose pulmonary vascular occlusions, and to detect alternative disease processes that require different treatments.

BRIEF DESCRIPTION OF THE DRAWINGS

FIG. 1 is an illustration of a respiratory system during inhalation.

FIG. 2 is an illustration of a respiratory system during exhalation.

FIG. 3 is an illustration of a respiratory system afflicted with a pulmonary vascular occlusion during exhalation.

DETAILED DESCRIPTION

Figure 4:
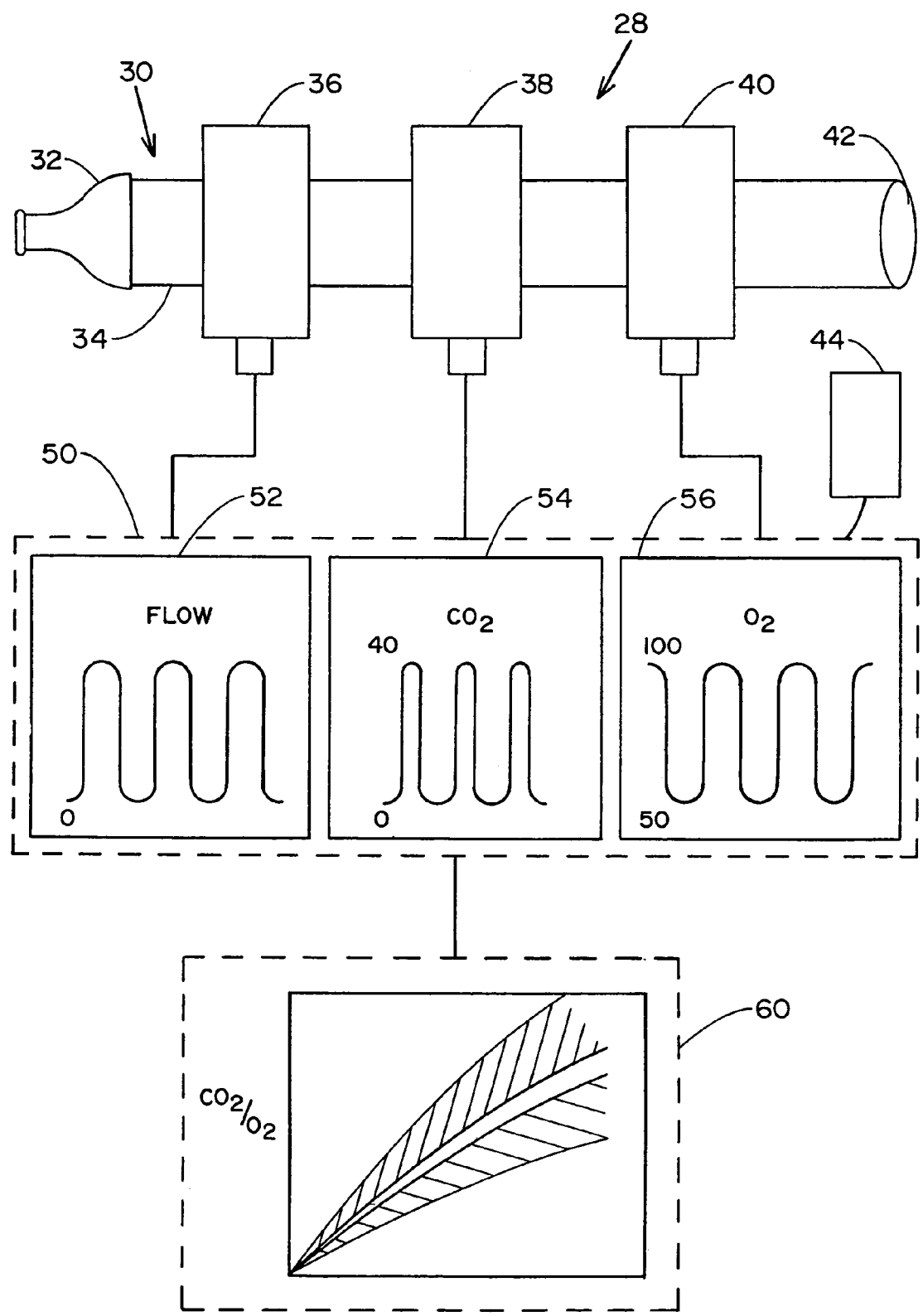
FIG. 4 is a schematic representation of the system of the present invention.

Referring now to the drawing in which like reference numerals refer to like parts throughout, there is seen in FIG. 1 a representation of lungs 10 free from any pulmonary occlusions. In healthy lungs 10, blood flows freely from the pulmonary arteries 12 into the capillaries 14 surrounding the individual alveoli 16 of the lungs 10. When inhaled air 18 is drawn into the lungs 10 and alveoli 16, oxygen is transferred from the inhaled air 18 to the blood stream and carbon dioxide is transferred out. Inhaled air 18 typically contains an oxygen partial pressure of approximately one hundred (100) torr and a carbon dioxide partial pressure of zero (0) torr.

Once the inhaled air 18 reaches the alveoli 16, the oxygen content decreases while the carbon dioxide content increases until an equilibrium with blood gas levels in the pulmonary arteries 12 is reached. The inhaled air 18 is then, as seen in FIG. 2, expired as exhaled air 20. Exhaled air 20 from properly functioning lungs typically contains a partial pressure of oxygen of about eighty (80) torr and a partial pressure of carbon dioxide of about forty (40) torr.

FIG. 3 depicts the functioning of a respiratory system afflicted with a pulmonary embolism 22 which, as an example, occludes blood flow to an afflicted lung 24. As a result, there is a reduction in the number of alveoli 16 that participate in gas exchange. This volume of space available in the alveoli 16 that is lost from participation is commonly referred to as alveolar deadspace. Due to the deadspace and loss of total alveolar volume available for gas exchange, afflicted lung 24 does not exchange gases as readily as the healthy lung 10. Accordingly, exhaled air 26 contains a higher partial pressure of oxygen and lower partial pressure of carbon dioxide than air exhaled from a healthy lung. In the example depicted in FIG. 3, exhaled air 26 exiting the respiratory system contains a partial pressure of oxygen of about eighty-five (85) torr and a partial pressure of carbon dioxide of about twenty (20) torr. Thus, the ratio of carbon dioxide to oxygen in exhaled air 26 from afflicted lung 24 (i.e., 20:85) is smaller than the ratio in exhaled air 20 from healthy lung 10 (i.e., 40:80) as seen in FIG. 2.

As seen in FIG. 4, a system 28 for measuring and diagnosing pulmonary disorders comprises a measuring unit 30 in combination with a data processing unit 50 and a display screen 60. Measuring unit 30 determines the overall flow of air inhaled into and exhaled out of the lungs while simultaneously determining the partial pressure of oxygen and carbon dioxide. Data processing unit 50 computes the concentrations of carbon dioxide, oxygen, and nitrogen from the partial pressures and determines the ratio of carbon dioxide to oxygen from the raw data obtained by measuring unit 30. The ratio of carbon dioxide to oxygen is then plotted against expired volume on display screen 60. By comparing the carbon dioxide ratios to average readings, the likelihood that a given patient has a pulmonary embolism can be determined.

Measuring unit 30 comprises a patient mouthpiece 32 connected in fluid communication to a breathing tube 34 having an open end 42 through which air can be inhaled or exhaled. Measuring unit 30 further comprises three sensors; a pneumotach 36, a capnometer 38, and an oxygen monitor 40. The three sensors are situated in series and in-line with breathing tube 34 for simultaneously measuring the flow, carbon dioxide, and oxygen levels of inhaled and exhaled air. Infrared and paramagnetic type sensors are preferred respectively. Sensors using spectrometric techniques may also work for both oxygen and carbon dioxide measurements providing they can supply data with rapid enough response time for breath-to-breath, real-time plotting. The mainstream technique for measuring the inhaled or exhaled air is preferred, but the sidestream technique may also be effective.

Figure 5:
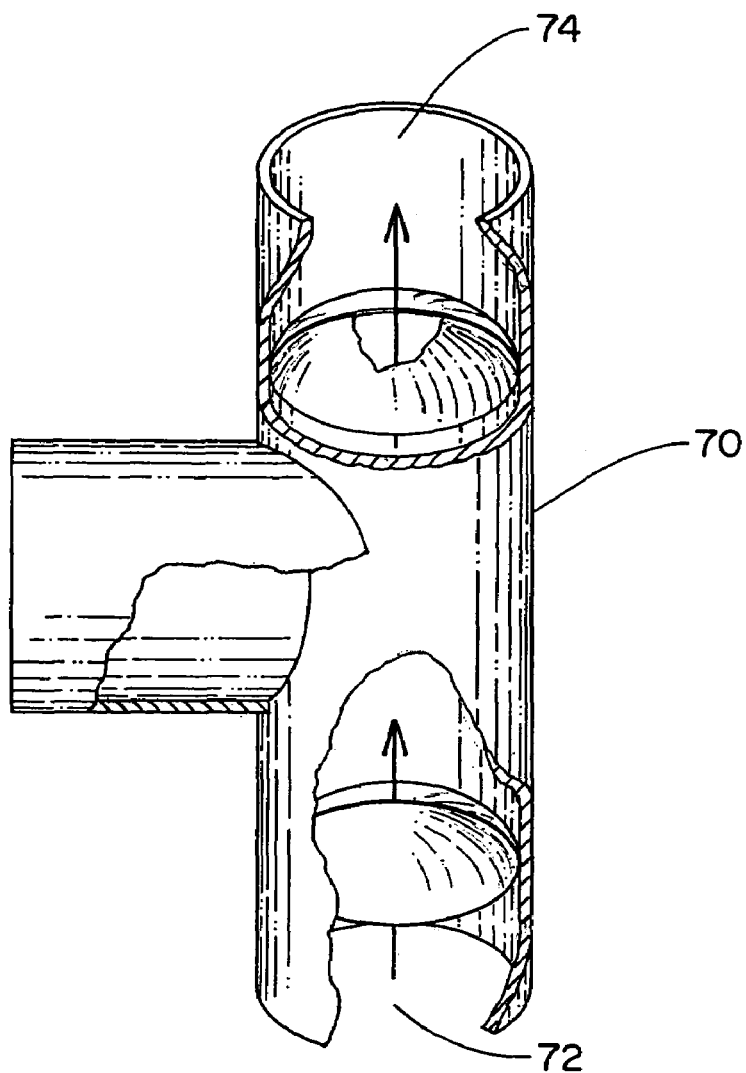
FIG. 5 is a perspective view of an attachment to the invention.

As seen in FIG. 5, a T-piece adaptor 70 may optionally be provided at open end 42 of breathing tube 34 for use with patients that are oxygen dependant. T-piece adapter 70 contains an inlet valve 72 and an outlet valve 74 which properly direct the passage of inhaled and exhaled air through the breathing tube 34. By connecting an oxygen dependant patient's supply to the intake valve 72, inhaled air can first be passed through the three sensors 36, 38, 40 to establish baseline readings of the oxygen and carbon dioxide concentrations for comparison to exhaled air, since an oxygen dependent patient receives air that has different concentrations than present in ambient air.

Data processing unit 50 comprises a commercially available computer processor programmed with software for the interpretation of the data obtained from measuring unit 30 and background comparison data. Software can be specifically developed to perform the necessary calculations to determine the partial pressures and carbon dioxide to oxygen ratios or software can optionally be purchased commercially and, if necessary, modified to run the appropriate algorithms. After additional research, the background comparison data can be updated based on data obtained from use of the invention to further refine expected normal values.

Display screen 60 comprises a cathode ray tube, plasma screen, or other visual display for displaying computerized data. Screen 60 can optionally display graphs representing predetermined reference or background data for test populations against which the current readings can be plotted for a visual comparison. In addition to displaying the carbon dioxide to oxygen ratios as a function of time calculated by data processing unit 50, screen 60 may optionally display a plot of the expired oxygen and carbon dioxide partial pressures. Using this display, a physician may estimate the efficiency of alveolar ventilation in patients with acute respiratory distress syndromes to assist in deciding the mechanical ventilation settings.

In addition to the three primary sensors 36, 38, 40, data processing unit 50 may optionally be connected to a pulse oximeter 44 that measures arterial oxygen saturation of hemoglobin in the arterial blood. From these data, and the additional measurement of pH and hemoglobin concentration in a peripheral venous blood sample, the cardiac output of the patient can be calculated according to the Fick equation. In order to perform the Fick equation, the average total oxygen consumed, the arterial oxygen content and venous oxygen content must be determined. The average total oxygen consumed can be determined from the oxygen tension and flow curves over a predetermined time period. For the purposes of determining cardiac output, a one minute time period is sufficient. The arterial oxygen content can be estimated by multiplying the arterial oxygen saturation (measured by pulse oximeter 44) by the hemoglobin concentration (determined from the venous blood sample). The venous oxygen content can be calculated by mathematical manipulation of the nadir (mean lowest) oxygen tension measured during deep expiration (in an awake patient) or a sign exhalation (in a mechanically ventilated patient) over the predetermined time period. From the nadir oxygen tension, venous oxygen saturation can be estimated according to published oxygen binding curves for the measured pH. The venous oxygen content is then calculated by multiplying the venous oxygen saturation by the venous hemoglobin (measured from the venous blood sample). Once these calculations have been made, the cardiac output is determined by dividing the total oxygen consumed by the difference between the arterial oxygen content and the venous oxygen content. The algorithm for the Fick calculation can be programmed into the data processing unit software and the results displayed on screen 60. The cardiac output measurement is useful for assisting the physician in determining the success or failure of treatment designed to relieve pulmonary vascular obstructions, or to treat circulatory shock.

Device 28 is used by having a patient breathe (inhale and exhale a predetermined number of times in succession) through mouthpiece 32 of the measuring unit 30. As the patient inhales and exhales the pneumotach flow sensor 36, capnometer 38, and oxygen monitor 40 perform their respective readings, which are then electrically transmitted via wires or cabling to data processing unit 50. The programmable software loaded into data processing unit 50 convert the measurements into volume and concentration readings, calculate the carbon dioxide to oxygen ratio, and display this ratio on screen 60 in the form of a graph against the volume of air expired. Readings may be optimized by requiring the patient to hold in inhaled air for several heartbeats before exhaling through the mouthpiece 32 of the measuring unit 30. It has been determined through testing that patients without a pulmonary embolism will normally have a carbon dioxide to oxygen ratio of 0.30 or greater while patients with a pulmonary embolism will have a carbon dioxide to oxygen ratio of 0.25 or less.

Figure 6:
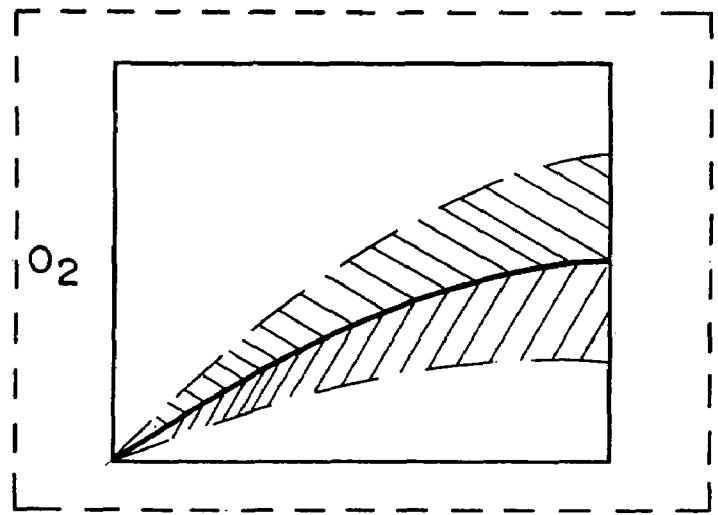
FIG. 6 is an illustration of a display screen readout.

Device 28 may also be used for the detection of whole-body oxygen consumption and determination of the adequacy of oxygen delivery during resuscitation from shock. During conditions of systemic inflammation the body will extract oxygen at higher levels than normal, resulting in an increase in the partial pressure of carbon dioxide-to-oxygen ratio in exhaled air. By using T-piece 70 in the manner explained above, the concentration of the oxygen provided to the patient and the concentration of the oxygen exhaled can be determined. As illustrated in FIG. 6, when the level of oxygen delivery (i.e., the amount provided minus the amount exhaled) observed at two inspired oxygen concentrations reaches normal levels a physician has visual conformation that the resuscitation performed is adequate. One method of determining the adequacy of resuscitation is to determine oxygen delivery at both relatively low fixed concentrations of oxygen and at relatively high fixed concentration. Relatively low concentrations include from about twenty-one to thirty percent (21-30%) oxygen and relatively high oxygen concentrations involve about forty-five to one hundred percent (45-100%) oxygen. The difference between oxygen delivery at relatively low concentrations verses relatively high concentrations can be compared against a nomogram for healthy patients of similar age, body mass, body mass index, and gender and used to assess the adequacy of fluid and vasopressor resuscitation.

Data processing unit 50 can additionally be programmed to display on screen 60 any of the individual measurements taken by sensors 36, 38, 40, and 44, or combinations thereof for diagnostic purposes. For example, a plot of the expired carbon dioxide and oxygen concentration over time could be used to estimate the efficiency of alveolar ventilation in patients with acute respiratory distress syndrome. Additionally, the plotted data from sensors 36, 38, 40, and 44 could be used to assist in deciding how to properly adjust mechanical ventilators setting, such as the degree of positive end-expiratory pressure, minute ventilation, and peak inspiratory pressure settings, to optimize patient care. For example, data from sensors 36, 37, 40, and 44, can be plotted individually in patients who are being mechanically ventilated. By simultaneously plotting the partial pressures of oxygen and carbon dioxide as a function of volume of each breath, the amount of carbon dioxide released and percentage of oxygen extracted can be determined. If the barometric pressure is known or inputted into data processing unit 50, the efficiency of alveolar ventilation during each tidal volume breath can be calculated. This information can then be used to adjust mechanical ventilation to optimize alveolar efficiency or breathing alveolar ventilation efficiency.

The addition of spectroscopy to the present invention expands and enhances the range of detectable gases and improves diagnostic capabilities. For example, $CO_2$, $O_2$, NO, CO, and $O_3$ can be detected by mass spectrometry employing electron spray ionization followed by time-flight and mass analysis by a quadripole. Raman spectroscopy can also be used to detect all molecules. Grating spectrometry can be used to produce a wide range of wavelengths, which can be used to detect multiple gases simultaneously. Spectrometers are available from a variety of manufacturers and the selection and implementation of one suitable for use with the present invention would be apparent to one of ordinary skill in the art. For example, Ocean Optics Dunedin, Fla. manufactures a grating spectrometer that allows detection in the 200-1020 nm range. As is well known, a spectrographic sensor unit measures the percent transmission of the radiation to allow measurement of the partial pressure of certain gases in the absorption chamber.

Alternatively, laser diode spectrometry can be used for detection of more than one gas and can be used for determining the presence of various pathophysiological processes that are specific to certain disease states. Lasers employing antimonide diodes (AlGaAsSb or AlGaInP) operating in cavity ring-down vertical mode in the mid or near infrared or visible light spectrum, preferably at room temperature and ambient pressure in the 1-100 mW power range are sufficient. The optimal absolute detection path length will be approximately 10 cm, with a diode laser operating in cavity mode with enhancement of the monochromatic light signal by oscillation between a complete and partial dielectric reflecting surface to produce the equivalent of a 1 kilometer path length. It should be understood that the absolute path length may be increased by light reflection to increase diagnostic sensitivity, if necessary.

For laser spectrometry in the near infrared range, detection wavelengths will be 1390 nm for carbon dioxide ($CO_2$) and 760 nm for oxygen ($O_2$), nitric oxide (NO) at 1800 nm, carbon monoxide (CO) at 1570 nm. Laser spectrometry at these parameters allows detection of 80 ppm or less for each gas in question. Wavelengths in the mid-infrared spectra (1-20 micrometers), will offer increased sensitivity into the low ppb range, and allow detection of $O_3$ and may be achieved without the need for cryogenic cooling. Aliphatic and aromatic organic compounds, include methane, ethane, and benzene derivatives can also be detected at the near and mid-infrared ranges.

The sampling speed of a device according to the present invention is important to its diagnostic capabilities. In a rapidly breathing subject, the exhalation phase may last only 500 mS. To accurately measure gas concentrations on a breath-by-breath basis, the response time of the emission-detection system must be calibrated to perform measurements of each of these gases on intervals not exceeding 50 mS. Each gas requires a specific wavelength, such that each discrete wavelength must be produced and measured either simultaneously, or produced and measured by alternating between the different wavelengths at a rate at or exceeding 20 Hz for each wavelength. This method may require simultaneous functioning of multiple light emitting diodes configured in parallel, spiral, or serial arrangement. Alternatively, the wavelength of a particular diode can be varied by changing the diode temperature, the current input, or the wavelength of the excitation source. As further research may reveal the significance of other volatile inorganic and organic compound gases to serve as adjuncts to the chemical analyses of the breath, additional diodes may be incorporated, or existing diodes tuned/modified, to allow detection of volatile aliphatic and aromatic organic molecules. For example, patients with emphysema are known to expire increased concentrations of ethane and the incorporation of an appropriate diode for measuring expired ethane would assist in the diagnosis of this disease. Simultaneous measurement of multiple volatile organic compounds has also been found to accurately diagnose the presence of lung cancer.

For laser detection of $CO_2$, $O_2$, NO, CO, and $O_3$, and like inorganic molecules, sensitivity requirements may mandate reflection of the laser beam across two mirrors, such that the light source and detection source cannot be feasibly mounted on the flow tube and the flow tube remain small and lightweight.

Figure 7:
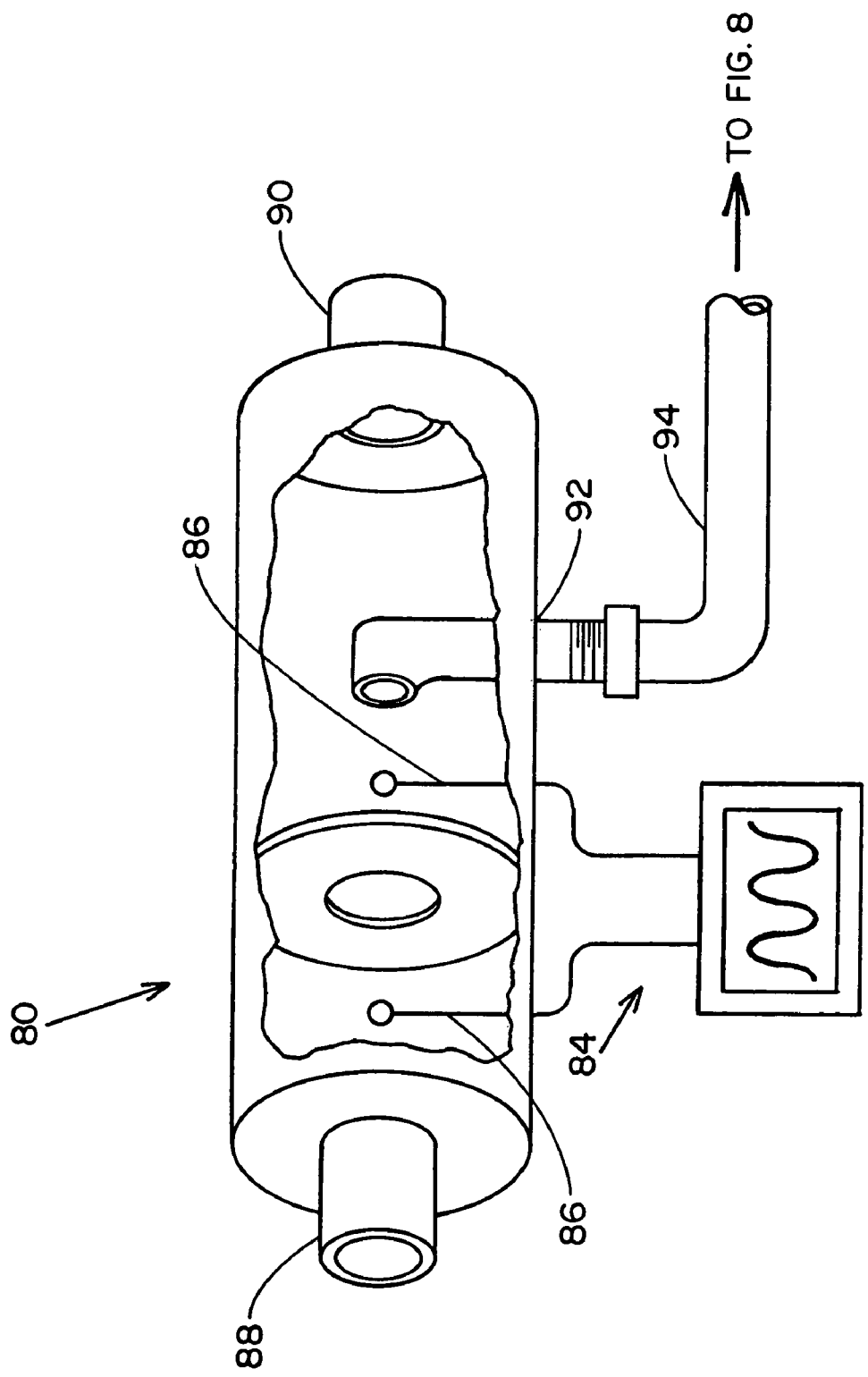
FIG. 7 is a schematic representation of a first portion of an alternative embodiment of the present invention.
Figure 8:
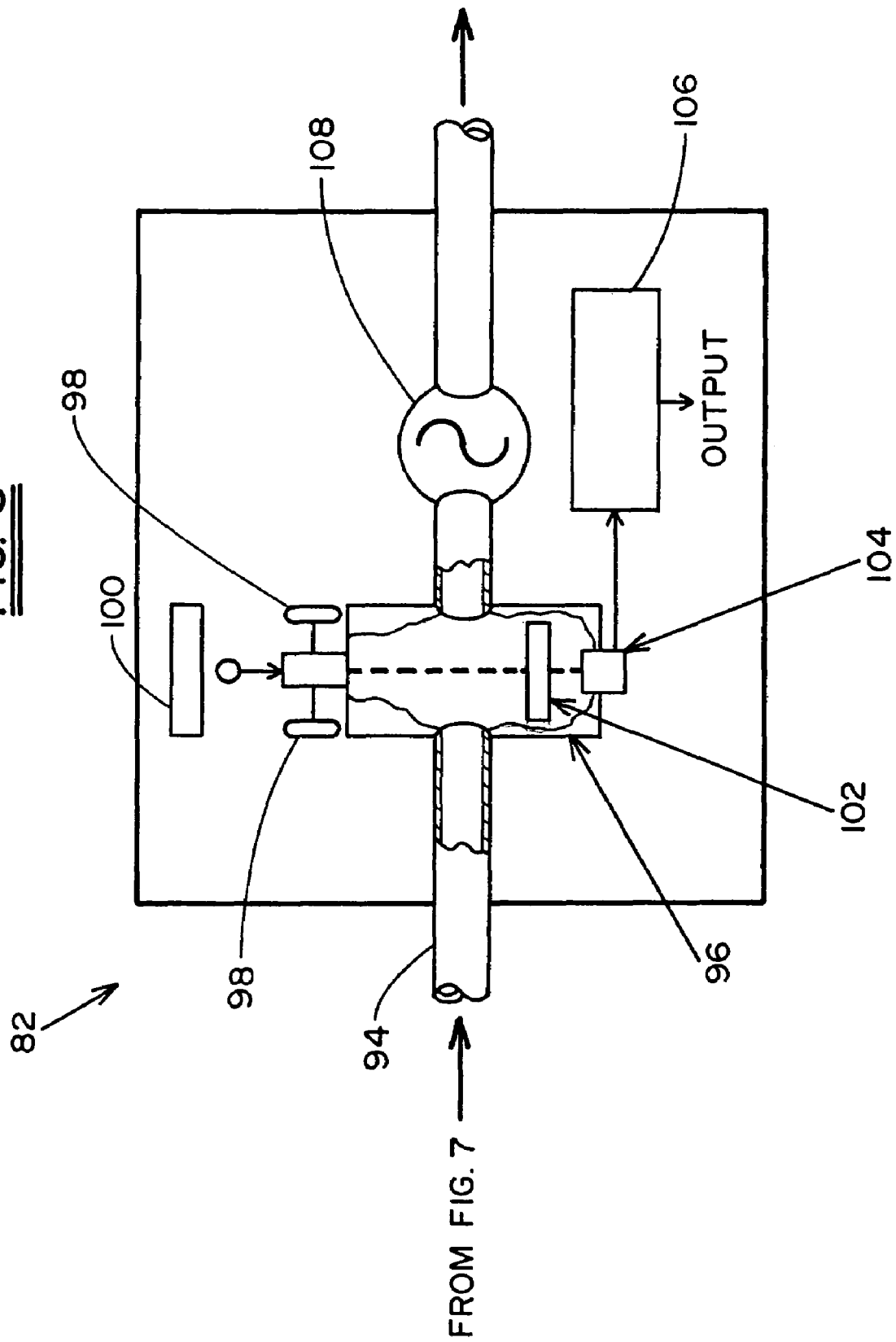
FIG. 8 is a schematic representation of a second portion of the alternative embodiment of FIG. 7.
Figure 9:
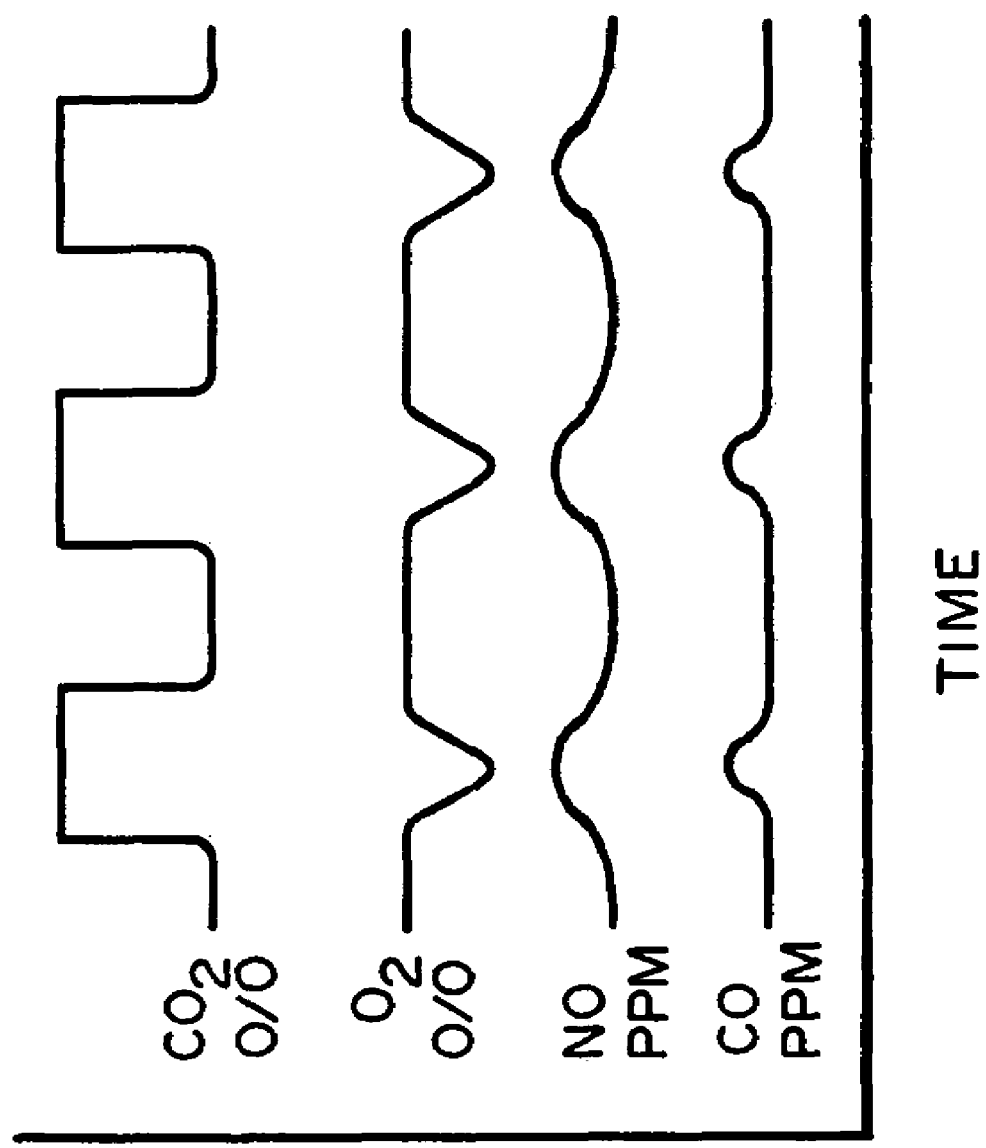
FIG. 9 is an illustration of a display screen readout.

Referring to FIGS. 7 and 8, an alternative an alternative embodiment of the present invention comprises a flow tube 80 and a separate analysis unit 82. Referring to FIG. 7, gas from an expired breath will pass through lightweight flow tube 80 where flow can be monitored by a sensor device 84 that operates using either ultrasonic pulse detectors 86, see U.S. Pat. Nos. 5,419,326, 5,503,151, 5,645,071, and 5,647,370, hereby incorporated by reference, or similar devices employing thermal-based or pressure-based sensor apparatuses.

Flow tube 80 includes an internal diameter sufficient to prevent restriction to expiration at up to 500 liters per minute (approximately 1.5 mm). Flow tube further includes ends 88 and 90 for connecting to standard coupling devices used on endotracheal tubes in the clinical setting. Flow tube 80 further includes a port 92 from which a gas sample can be diverted through vacuum aspiration at a rate of approximately 10-100 mL/min to central analysis unit 82. Gas is conveyed from port 92 by a flexible tube 94 having an internal diameter of approximately 3-5 mm and manufactured from plastic, polyethylene, Teflon®, or other polymeric material.

As seen in FIG. 8, flexible tube 94 interconnects flow tube 80 to an analyzing chamber 96 in central analysis unit 82. Analyzing chamber 96 further includes a laser diode 98, total reflecting mirror 100, partial reflecting mirror 102, and light detector cell 104 for performing laser spectroscopy. FIG. 8 depicts a single diode 98 that may be tuned to different wavelengths, although multiple diodes could be used if desired.

Analysis unit 82 further includes data processor 106 interconnected to light detector cell 104. The process of aspirating gas from flow tube 80 to the analyzing chamber 96 may result in a several second delay between flow data generated by sensor device 84 and corresponding data generated from measurements in analyzing chamber 96. The computerized processing must therefore correct for the delay to align the plots of expired gases as a function of time accurately, and as a function of each other, and with respect to time. Data processor 106 is therefore programmed to precisely align, for example, the measured initial $CO_2$ rise with the initial $O_2$ drop, such that the ratio of each gas can be plotted as a continuous measurement throughout the entire exhaled breath. Analysis unit 82 may include a vacuum pump 108 for controlling the amount of air withdrawn from flow tube 80.

Figure 11:
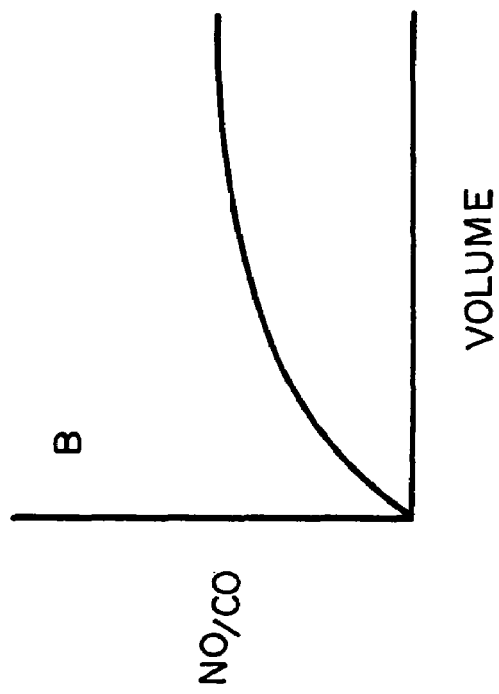
FIG. 11 is an illustration of a display screen readout.
Figure 10:
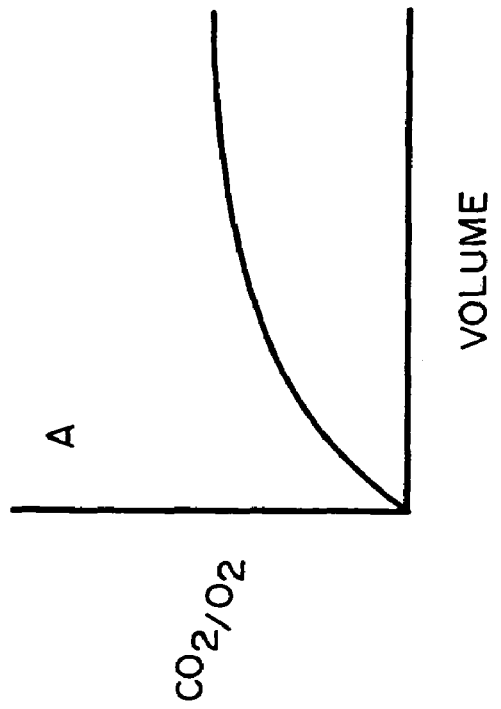
FIG. 10 is an illustration of a display screen readout.

As seen in FIG. 10, the $CO_2/O_2$ ratio may then be plotted as a function of expired volume based on data obtained from flow tube 80 and analysis unit 82. This is accomplished by initiating the inflection of the $CO_2/O_2$ ratio rise coincident with the mean transit time required to transport the gas sample from the inlet port to the central analyzer unit added to exact time that expired flow initiated with each breath. The maximum expired $CO_2$ can be plotted as a function of the maximum $O_2$, and the location of this point on a two-dimensional plot can assist in the diagnosis of pulmonary vascular occlusion versus other causes of ventilation-perfusion mismatch. The same analyses and plots can be done for the NO/CO ratio, as seen in FIG. 11.

Figure 12:
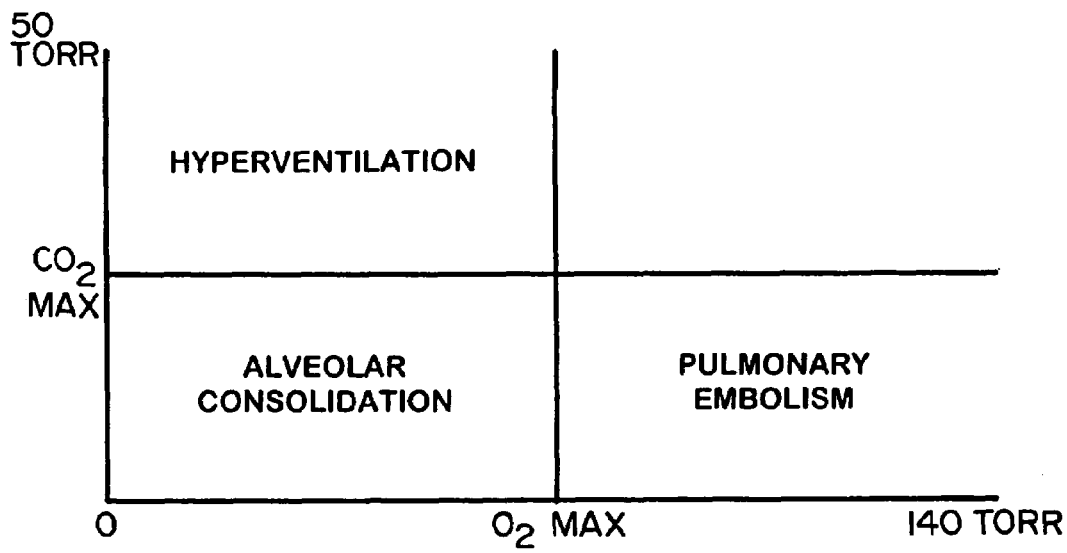
FIG. 12 is an illustration of a display screen readout.
Figure 13:
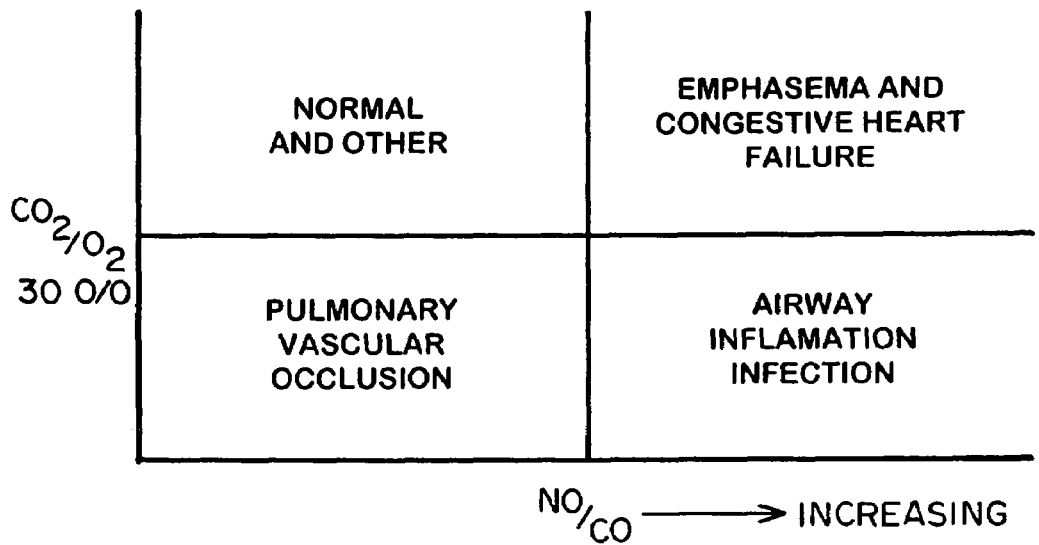
FIG. 13 is an illustration of a display screen readout.
Figure 14:
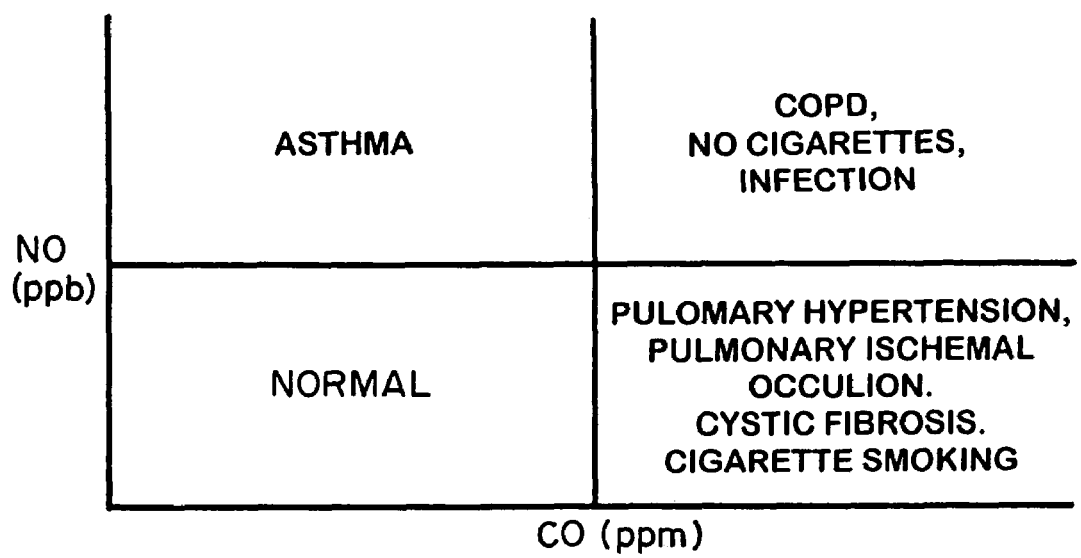
FIG. 14 is an illustration of a display screen readout.
Figure 15:
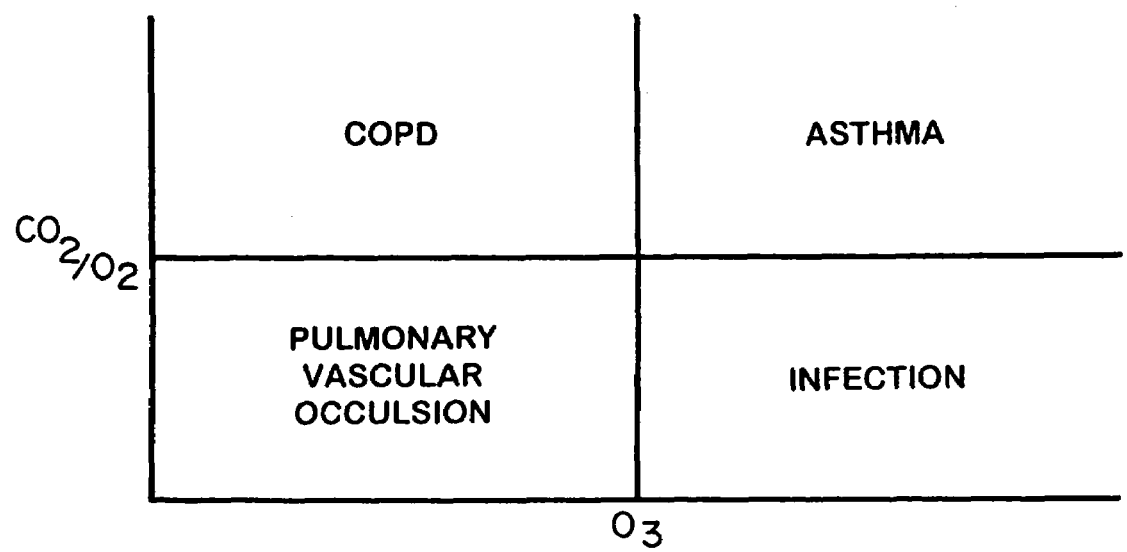
FIG. 15 is an illustration of a display screen readout.

In addition to plotting the various $CO_2/O_2$ and NO/CO ratios independently, the ratio of $CO_2$ may be plotted against $O_2$ and $CO_2/O_2$ may be plotted as a function of NO/CO, as seen in FIGS. 12 and 13. The location of the plots can help to distinguish certain disease processes as depicted in FIGS. 12-14. Ozone can be plotted in a similar manner relative to $CO_2/O_2$, as seen in FIG. 15. The $CO_2:O_2$ measurement enhances the specificity of diagnosis, which is important to measure the NO concentration in view of the apparent V/Q relationship of the lung. A very high NO concentration with a high $CO_2:O_2$ ratio (>0.45) is far more likely to represent hypoventilation with inflammation of the airways together with obstruction to outflow. In contrast, a high NO concentration with a low $CO_2:O_2$ ratio (e.g., <0.3) indicates that airways are not obstructed, and that NO production could be the result of infection. Additionally, the simultaneous measurement of CO further enhances the specificity of the device. Very few disease processes cause the combination of a low $CO_2:O_2$, a high CO and a low NO concentration. These plots are used to predict the presence of certain diseases as depicted. The expected cutoff to distinguish and abnormally high NO concentration will be approximately 10 ppb, and similarly, the cutoff for CO will be approximately 5-10 ppm.

What is claimed is:

1. A system for non-invasively diagnosing abnormal respiratory function, comprising:
    a patient breathing tube;
    a flow meter connected to said tube;
    a spectrometer interconnected to and in fluid communication with said tube, wherein said spectrometer is adapted to detect the concentration of gases present in said tube; and
    data processing means interconnected to said flow meter and said spectrometer, wherein said data processing means is programmed to calculate and display at least one gas concentration ratio selected from the group consisting of the ratio of NO relative to the concentration of CO, the ratio of $CO_2$ to $O_2$ relative to the ratio of NO to CO, the ratio of NO to CO relative to expired volume, the ratio of $CO_2$ to $O_2$ relative to the ratio of $CO_2$ to $O_2$ relative to expired volume, and the ratio of $CO_2$ to $O_2$ simultaneously with a plot of NO relative to expired volume.

2. The system of claim 1, wherein said gas concentration ratio is the concentration of $CO_2$ relative to the concentration of $O_2$.

3. The system of claim 1, wherein said gas concentration ratio is the concentration of NO relative to the concentration of CO.

4. The system of claim 1, wherein said gas concentration ratio is the ratio of $CO_2$ to $O_2$ relative to the ratio of NO to CO.

5. The system of claim 1, wherein said gas concentration ratio is the ratio of NO to CO relative to expired volume.

6. The system of claim 1, wherein said gas concentration ratio is the ratio of $CO_2$ to $O_2$ relative to NO.

7. The system of claim 1, wherein said gas concentration ratio is the ratio of $CO_2$ to $O_2$ simultaneously with a plot of NO relative to expired volume.

8. The system of claim 1, wherein said spectrometer comprises a laser diode spectrometer remotely interconnected to and in fluid communication with said tube via a port in said patient breathing tube.

9. The system of claim 8, further comprising a vacuum pump interconnected to said spectrometer and said port.

10. The system of claim 9, wherein said vacuum pump operates at a rate of between about 10 to 100 milliliters per minute.

11. The system of claim 8, wherein said laser diode spectrometer is adapted to measure analyte concentrations of NO, CO, $CO_2$, and $O_2$.

12. The system of claim 8, wherein said laser diode spectrometer simultaneously measures $CO_2$, $O_2$, NO and CO.

13. The system of claim 8, wherein said laser spectrometer alternates between the measurement of any combination of $CO_2$, $O_2$, NO, and CO at a rate of at least twenty times per second for each such molecule.

14. The system of claim 8, wherein said laser spectrometer comprises a monochromatic light source from at least one tunable diode laser operating in a ring-down cavity mode with two or more mirror to increase apparent path length.

15. The system of claim 8, wherein said tube further includes a coupling for attachment to standard ventilator circuits.

16. The system of claim 8, wherein said tube further includes a coupling for attachment to a patient mouthpiece.

17. The system of claim 8, wherein said flow meter is a sensor selected from the group consisting of thermal flow sensors, pressure differential sensors, and ultrasonic flow sensors.

18. A system for non-invasively diagnosing abnormal respiratory function, comprising:
   a patient breathing tube;
   a flow meter connected to said tube;
   a spectrometer interconnected to and in fluid communication with said tube, wherein said spectrometer is adapted to detect the concentration of gases present in said tube; and
   data processing means interconnected to said flow meter and said spectrometer, wherein said data processing means is programmed to phase align the concentrations of said gases to allow for accurate plotting of ratios and concentrations as a function of expired volume.

19. A system for non-invasively diagnosing abnormal respiratory function, comprising:
   a patient breathing tube;
   a flow meter connected to said tube;
   a spectrometer interconnected to and in fluid communication with said tube, wherein said spectrometer is adapted to detect the concentration of gasses present in the tube; and
   data processing means interconnected to said flow meter and said spectrometer, wherein said data processing means is programmed to calculate and display the ratio of CO2 to O2 relative to expired volume.

* * * * *

UNITED STATES PATENT AND TRADEMARK OFFICE
CERTIFICATE OF CORRECTION

PATENT NO. : 7,445,601 B2  Page 1 of 1
APPLICATION NO. : 10/816279
DATED : November 4, 2008
INVENTOR(S) : Jeffrey A. Kline It is certified that error appears in the above-identified patent and that said Letters Patent is hereby corrected as shown below:

Column 11, Claim 1, line 1, please insert -- NO, -- between "to" and "the"

Signed and Sealed this

Twenty-fifth Day of August, 2009

David J. Kappos
*Director of the United States Patent and Trademark Office*